(12) United States Patent
Watanabe et al.

(10) Patent No.: US 8,809,053 B2
(45) Date of Patent: Aug. 19, 2014

(54) CARDIOMYOCYTE CULTURE SUPPORT

(75) Inventors: Masanao Watanabe, Tokyo (JP); Teruo Okano, Tokyo (JP); Masayuki Yamato, Tokyo (JP); Tatsuya Shimizu, Tokyo (JP); Yoshikatsu Akiyama, Tokyo (JP)

(73) Assignees: Dai Nippon Printing Co., Ltd., Tokyo (JP); Tokyo Women's Medical University, Tokyo (JP)

( * ) Notice: Subject to any disclaimer, the term of this patent is extended or adjusted under 35 U.S.C. 154(b) by 1072 days.

(21) Appl. No.: 12/186,572

(22) Filed: Aug. 6, 2008

(65) Prior Publication Data

US 2009/0098651 A1   Apr. 16, 2009

(30) Foreign Application Priority Data

Aug. 6, 2007   (JP) ................... 2007-204415

(51) Int. Cl.
   *C12N 5/07*   (2010.01)
(52) U.S. Cl.
   USPC ........................................ 435/402
(58) Field of Classification Search
   None
   See application file for complete search history.

(56) References Cited

U.S. PATENT DOCUMENTS 7,041,343 B1 *   5/2006   Nelles et al. ................... 428/1.1
7,083,834 B2 *   8/2006   Kuntz et al. ................... 428/1.1

FOREIGN PATENT DOCUMENTS

| JP | 6-104061 B2 | 12/1990 |
| JP | 8-278491 A | 10/1996 |
| WO | 97/00600 A2 | 1/1997 |

OTHER PUBLICATIONS

Fujita et al., Journal of Biomedical Optics 11(2), Mar./Apr. 2006.*
Yuji Haraguchi, et al.; "Electrical Coupling of Cardiomyocyte Sheets Occurs Rapidly via Functional Gap Junction Formation"; Biomaterials; 2006; pp. 4765-4774; vol. 27; Elsevier Ltd.
Japanese Office Action issued in application No. 2007-204415 issued May 15, 2012.
Kaneko, Tatsuo, "Liquid-crystal polymers and life science" Surface, 2006, vol. 44, No. 10, p. 390-402.

* cited by examiner

*Primary Examiner* — Allison Ford
*Assistant Examiner* — Yvonne Pyla
(74) *Attorney, Agent, or Firm* — Sughrue Mion, PLLC

(57) ABSTRACT

Methods and reagents are described for myocardial regenerative therapy using cardiomyocytes that are cultured ex vivo to have a controlled orientation of beating. This is achieved by growing the cardiomyocytes on a culture support that is coated with a polymerizable liquid crystal which is oriented so as to be in a liquid crystal phase state prior to curing with ionizing radiation or ultraviolet rays.

2 Claims, 1 Drawing Sheet

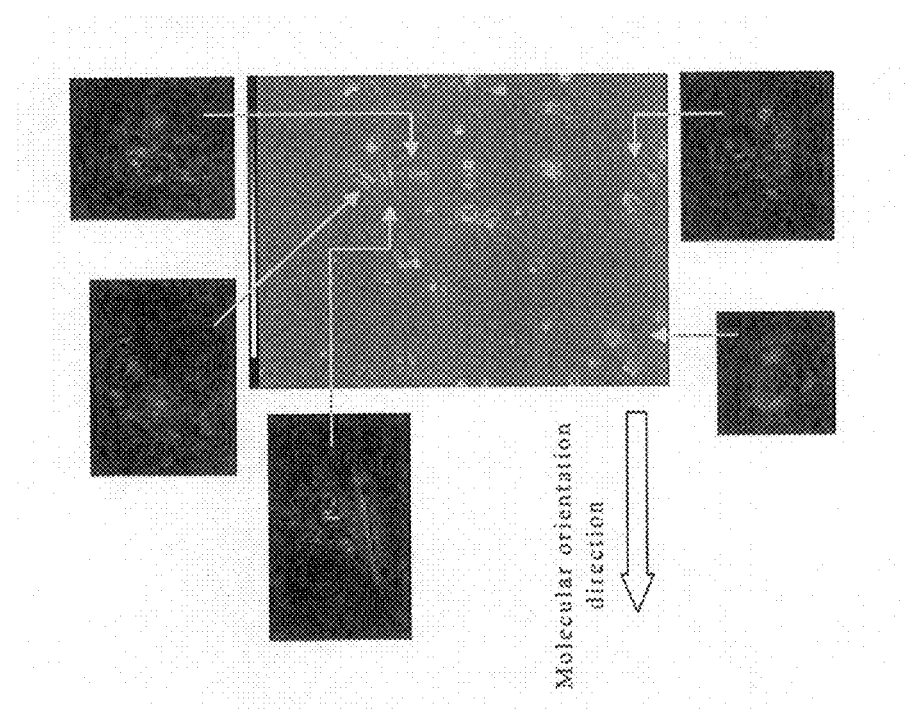

CARDIOMYOCYTE CULTURE SUPPORT

BACKGROUND OF THE INVENTION

1. Field of the Invention

The present invention relates to a cardiomyocyte culture support for controlling the orientation of beating of cardiomyocytes and a method for producing the same.

2. Background Art

A method for myocardium transplantation and for myocardial regenerative therapy wherein somatic stem cells (tissue stem cells) represented by bone marrow cell are selected and transplanted (injected) directly into the heart of a patient has so far been studied. In addition, there have been studies regarding the induction of efficient differentiation of ES cells (embryonic stem cells) of non-human mammals into cardiomyocytes. In recent years, there have also been studies regarding the efficient induction of differentiation of tissue stem cells (e.g., undifferentiated cells contained in fatty tissue) into cardiomyocytes. Thus, the range of cells that are used as sources for myocardium transplantation and myocardial regenerative therapy has been expanding. However, a technique for artificially constructing tissue having functions of the myocardium, such as the function of beating, has not yet been established.

A variety of cell culture supports for forming a sheet-type cell aggregate used for regenerative medicine and the like have been available (e.g., JP Patent Publication (Kokoku) No. 6-104061 B (1994) or Y. Haraguchi et al./Biomaterials 27 (2006) 4765-4774). However, unlike original myocardial tissue, cardiomyocyte sheets produced by the above techniques do not have orientation. In the case of a cardiomyocyte sheet prepared from primary cardiomyocytes (cells released from connective tissue (collected from a baby rat) by collagenase treatment) with the use of a conventional cell culture support, cardiomyocytes account for half of the cells dispersed therein, and vascular endothelial cells, fibroblast cells, and the like account for the other half thereof. A pacemaker cell can be found among 10,000 cardiomyocytes. Cells are electrically connected to each other via a gap junction on a cardiomyocyte sheet formed in a random manner. Accordingly, in a binding stage, the pathway for beating is established in a manner such that electric signals generated from a plurality of pacemaker cells are transmitted through cardiomyocytes and the other cells. In the case of a confluent cell sheet, synchronization takes place via the substantially shortest pathway involving pacemaker cells. However, in such case, electric signal emission lacks orientation. Thus, during beating, the entire sheet repeatedly dilates and contracts; however such dilation and contraction lack orientation.

SUMMARY OF THE INVENTION

In the case of the heart, the direction of transmission of action potentials generated at the sinoatrial node and the direction of contraction of left and right ventricles and atriums are predetermined. Thus, it has been necessary to provide myocardial tissue that can beat in a single direction for applications such as patch plasty for a heart experiencing heart failure to control the beat. Therefore, it is an objective of the present invention to provide a cardiomyocyte culture support used for obtaining cardiomyocytes having a controlled orientation of beating that are thus available for myocardial regenerative therapy, and to provide a method for producing the same.

As a result of intensive studies to achieve the above objective, the present inventors have found that, in the case that cardiomyocytes are cultured with the use of cardiomyocyte culture support having a cured polymerizable liquid crystal layer having a molecular oriented surface, the seeded cardiomyocytes adhere and resume beating along with the molecular orientation on the layer while retaining the capacity to beat.

Specifically, the present invention encompasses the following inventions.

(1) A cardiomyocyte culture support comprising a cured polymerizable liquid crystal layer having a molecular orientation on a surface thereof.

(2) The cardiomyocyte culture support according to (1), wherein the cured polymerizable liquid crystal layer is formed on a base material having orientation ability.

(3) The cardiomyocyte culture support according to (2), wherein the base material comprises a substrate and an oriented film on the substrate, and the cured polymerizable liquid crystal layer is formed on the oriented film.

(4) The cardiomyocyte culture support according to any one of (1) to (3), wherein the cured polymerizable liquid crystal layer is a cured layer comprised of nematic liquid crystal having at least two polymerizable groups in each liquid crystal molecule.

(5) A method for producing a cardiomyocyte culture support, comprising the steps of:

applying a coating solution comprising a polymerizable liquid crystal on a base material having orientation ability so as to form a coating film;

allowing the polymerizable liquid crystal comprised in the coating film to be oriented so as to be in a liquid crystal phase state; and forming a cured polymerizable liquid crystal layer by irradiating the coating film with ionizing radiation or ultraviolet rays so as to cure the polymerizable liquid crystal in a liquid crystal phase state by polymerization.

(6) The method for producing a cardiomyocyte culture support according to (5), wherein the base material comprises a substrate and an oriented film on the substrate, and the coating solution is applied on the oriented film.

(7) The method for producing a cardiomyocyte culture support according to (5) or (6), wherein the polymerizable liquid crystal is a nematic liquid crystal having at least two polymerizable groups in each liquid crystal molecule.

(8) The method for producing a cardiomyocyte culture support according to any one of (5) to (7), wherein the coating solution further comprises a photopolymerization initiator, and the polymerizable liquid crystal in a liquid crystal phase state is polymerized by irradiating the coating film with ultraviolet rays.

(9) A method for culturing cardiomyocytes, comprising the step of culturing cardiomyocytes on a cured polymerizable liquid crystal layer of the cardiomyocyte culture support according to any one of (1) to (4).

(10) A cardiomyocyte-adherent substrate comprising a cured polymerizable liquid crystal layer having a molecular orientation on a surface thereof, wherein cardiomyocytes are adhered to the surface, and beating direction of the cardiomyocytes is controlled in accordance with the molecular orientation of the surface of the cured polymerizable liquid crystal layer.

(11) A cardiomyocyte aggregate having controlled beating direction obtained by culturing the cardiomyocyte on the surface of a cured polymerizable liquid crystal layer having a molecular orientation.

Effects of the Invention

Cardiomyocytes having a controlled orientation of beating can be obtained by culturing cardiomyocytes with the use of the cardiomyocyte culture support of the present invention.

This specification incorporates the content of the specification of Japanese Patent Application No. 2007-204415, for which priority is claimed to the present application.

BRIEF DESCRIPTION OF THE DRAWINGS

FIG. 1 shows a result of motion video analysis of contracting cardiomyocytes cultured on the cardiomyocyte culture support of the present invention, which is recorded at 1/30 s and is analyzed by the software that can show an interframe difference.

DESCRIPTION OF THE PREFERRED EMBODIMENTS

An embodiment of the method for producing a cardiomyocyte culture support of the present invention is hereinafter described.

First, a coating solution comprising a polymerizable liquid crystal is applied to a base material having orientation ability such that a coating film is formed. Known techniques can be used as application methods whereby a coating solution can be applied to a substrate. Specific examples thereof include a roll coating method, a gravure coating method, a slide coating method, and an immersion method. In addition, in order to improve adhesion between a base material and a coating film, a coating solution may be applied to an adhesive layer after providing a base material with such adhesive layer in a manner described in JP Patent Publication (Kokai) No. 8-278491 A (1996).

Next, the coating film formed on the base material is maintained at a certain temperature at which a liquid crystal structure is expressed as a result of the orientation of a polymerizable liquid crystal (hereinafter a state in which a liquid crystal structure is expressed is referred to as a liquid crystal phase state). In such state, the coating film is exposed to ionizing radiation or ultraviolet rays such that the polymerizable liquid crystal is polymerized and cured. As a result of such step, a cured polymerizable liquid crystal layer having a molecular orientation is formed. The term "molecular orientation" used herein refers to a state in which molecules, each of which is a structural unit that constitutes a substance, are aligned in a specific direction in a preferential manner.

In addition, it is common to mix a levelling agent with a polymerizable liquid crystal and smooth the surface of a cured polymerizable liquid crystal layer when a general optical material is prepared. However, according to the present invention, it is preferable not to use a levelling agent because it is important for the outermost surface of a cured polymerizable liquid crystal layer to have a molecular orientation. Meanwhile, as long as cells cultured on the surface of a cured polymerizable liquid crystal layer can be influenced by the molecular orientation on the surface thereof, another reagent or the like may be applied to the surface and a certain type of a membrane or film may be formed on the surface. Thus, also in a case in which a cell culture medium is provided on a cured polymerizable liquid crystal layer, the resulting product is also encompassed in the cardiomyocyte culture support of the present invention.

Regarding a method for curing a polymerizable liquid crystal, in the case of using a three-dimensional crosslinking method, for instance, a photopolymerization initiator is added to liquid crystal molecules, followed by ultraviolet ray irradiation for curing. In addition, a method comprising direct ionizing radiation (e.g., electron beam irradiation) for curing may be used.

When ultraviolet rays are used, the exposure dose depends on the polymerizable liquid crystal material to be used. However, in general, the exposure dose is preferably approximately 200 to 400 mJ/cm$^2$. The exposure wavelength is preferably approximately 200 to 450 nm. In addition, in the case of electron beam exposure, the dose is preferably 50 to 500 Gy.

A preferable base material used in the present invention is a base material having orientation ability that allows a polymerizable liquid crystal applied to the base material to express a molecular orientation. Examples of such base material having orientation ability include a base material obtained by subjecting a substrate to an orientation treatment and a base material comprising a substrate having orientation ability.

In the case of a base material obtained by subjecting a substrate to an orientation treatment, a various orientation can be realized and a further effective orientation can be achieved by selecting an orientation treatment. Examples of a method for subjecting a substrate to an orientation treatment include: a method wherein an oriented film is laminated on a substrate; and a method wherein a resin film laminated on a substrate and is subjected to a rubbing or polarization treatment such that an oriented film is formed. As such an oriented film, in general, an oriented film used for a liquid crystal display apparatus and the like can be preferably used. Examples of a generally used oriented film include resin films such as a polyimide film, a polyamide film, and a polyvinyl alcohol film. In addition, for a rubbing treatment, the following method is generally used: a method for rubbing a resin film with a rubbing cloth, comprising the steps of: wrapping a metal roll with a rubbing cloth selected from materials such as rayon, cotton, polyamide, and polymethylmethacrylate; and allowing the roll to rotate while it remains in contact with a resin film or transferring a substrate having a resin film on the roll at a fixed position. In addition, it is also possible to impart orientation ability via polarized irradiation with the use of a photo-oriented film. In the case of a resin substrate, it is also possible to obtain a base material having orientation ability by subjecting the surface of a substrate itself to an orientation treatment such as a rubbing treatment.

A commercially available resin for oriented film may be used for the oriented film formation. For instance, SUN-EVER® (Nissan Chemical Industries, Ltd.), an AL series film (JSR Corporation), LIXON® aligner (Chisso Corporation), or the like is applied to a substrate and an orientation treatment may be carried out in the above manner.

Examples of a material for a substrate include; glass materials such as glass, quartz glass, fused quartz, synthetic quartz, alumina, sapphire, ceramics, forsterite, and photosensitive glass; silicon materials such as single crystal silicon, amorphous silicon, silicon carbide, silicon oxide, and silicon nitride; resins (e.g., a polycarbonate resin, a polyester resin such as polyallylate or polyethylene terephthalate, a polyimide resin, a polysulfone resin, a polyethersulfone resin, a polystyrene resin, a polyolefin resin such as polyethylene or polypropylene, a polyvinyl alcohol resin, a cellulose acetate resin, a polyvinyl chloride resin, and a polymethyl methacrylate resin); and metals (e.g., stainless, nickel, titanium, and aluminum).

Examples of a base material having orientation ability include a base material that is a stretched film. With the use of such a stretched film, it is possible to allow a polymerizable liquid crystal to be oriented along with the stretching direction. A commercially available stretched film may be used as such a stretched film. In addition, it is also possible to form a stretched film made of various materials according to need. Examples of a material for such a stretched film include materials similar to the above resins used as materials for a substrate.

A polymerizable liquid crystal used in the present invention is not particularly limited as long as it is a polymerizable liquid crystal with which a liquid crystal phase having nematic or smectic regularity can be formed. Nematic liquid crystal materials can be preferably used. Among nematic liquid crystals, a nematic liquid crystal comprising liquid crystal molecules each containing at least two polymerizable groups can be preferably used. For instance, a polymerizable liquid crystal disclosed in JP Patent Publication (Kohyo) No. 11-513019 A (1999) can be used, such polymerizable liquid crystal being represented by the following general formula:

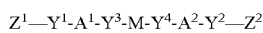

$Z^1—Y^1-A^1-Y^3-M-Y^4-A^2-Y^2—Z^2$ wherein alphabetical references have the following meanings: $Z^1$ and $Z^2$ each represent a reactive group that can induce polymerization, such as $C_1$-$C_4$ alkenyl group, and particularly a vinyl group, or a 1-methylvinyl group; $Y^1$ to $Y^4$ each represent a chemical single bond, oxygen, sulfur, —O—CO—, —CO—O—, —OCO—O—, —CO—NR—, —NR—CO—, —O—CO—NR—, —NRCO—O—, or —NR—CO—NR— (provided that at least one of $Y^3$ and $Y^4$ represents —O—CO—O—, —O—CO—NR—, —NR—COO—, or —NR—CO—NR—); $A^1$ and $A^2$ each represent a spacer having 2 to 30 carbon atoms (provided that a carbon chain may be cleaved with oxygen in an ether functional group, sulfur in a thioether functional group, a nonneighboring imino group, or a $C_1$-$C_4$ alkylimino group); M represents a mesogen group; and R represents a $C_1$-$C_4$ alkyl group.

In addition, a compound represented by the following general formula (1) can be preferably used:

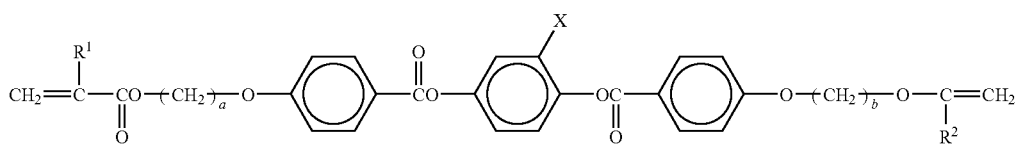

(1)

wherein $R^1$ and $R^2$ each represent a hydrogen or methyl group, X represents hydrogen, chlorine, bromine, iodine, a $C_1$-$C_4$ alkyl group, a methoxy group, a cyano group, or a nitro group, a and b each represent a different integer from 2 to 12.

Regarding a compound represented by the general formula (1), preferably, $R^1$ and $R^2$ each represent hydrogen because of the wide temperature range in which a liquid crystal phase is expressed. In addition, preferably, X represents chlorine or a methyl group. Further, a and b, each of which represents a chain length of an alkylene group that serves as a spacer before a (meth)acryloyloxy group and an aromatic ring (separately located at both ends of a molecule chain), each represent a different integer from 4 to 10, more preferably from 6 to 9. A compound represented by the general formula (1), where at least one of a and b represents 1 or more, is stable and unlikely to be hydrolyzed. In addition, such compound itself has low crystallinity. When a and b each represent 12 or less, the isotropic transition temperature (isotropic phase transition temperature) becomes high. Due to such reasons, a compound represented by the above formula, where a and b each represent particularly from 2 to 12, is advantageous in terms of the wide temperature range in which liquid crystallinity is expressed.

Also, specific examples of a polymerizable liquid crystal include the compounds listed below.

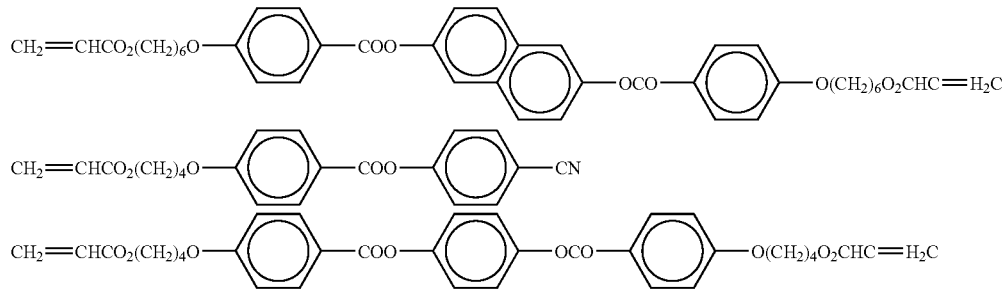

-continued

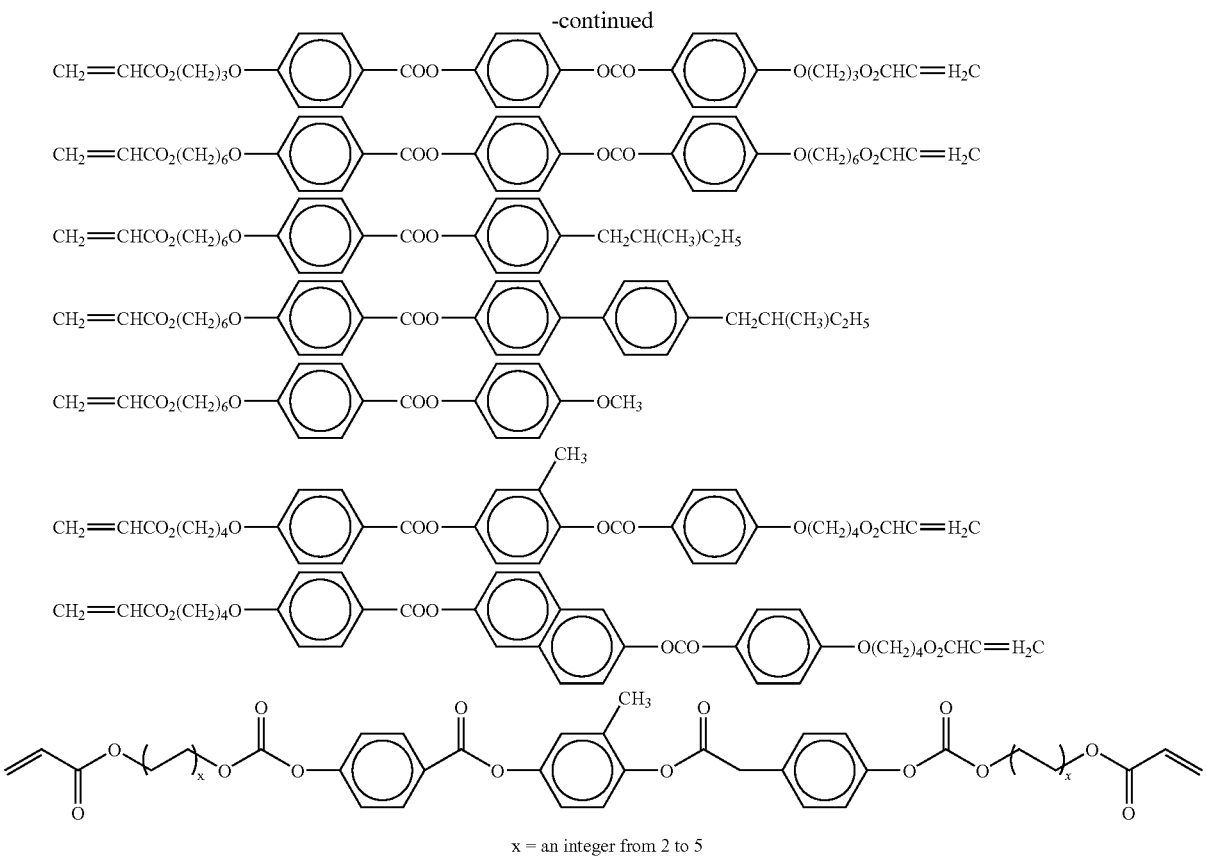

x = an integer from 2 to 5

For a polymerizable liquid crystal, a polymerizable monomer molecule, a polymerizable oligomer molecule, a polymerizable polymer molecule, and the like may be used alone or in combinations of two or more thereof. Also, a commercially available material may be used. Examples thereof include RMM34® (Merck) and LC242® (BASF).

According to the present invention, preferably, a coating solution containing a polymerizable liquid crystal may further contains a photopolymerization initiator. A photopolymerization initiator that can be preferably used is a radical polymerization initiator. A radical polymerization initiator generates free radicals upon application of ultraviolet energy or the like. Examples thereof include benzyl (also referred to as bibenzoyl), benzoin isobutyl ether, benzoin isopropyl ether, benzophenone, benzoylbenzoic acid, methyl benzoylbenzoate, 4-benzoyl-4'-methyldiphenyl sulfide, benzylmethylketal, dimethylaminomethyl benzoate, 2-n-butoxyethyl-4-dimethylaminobenzoate, isoamyl p-dimethylaminobenzoate, 3,3'-dimethyl-4-methoxybenzophenone, methylbenzoylformate, 2-methyl-1-(4-(methylthio)phenyl)-2-morpholinopropane-1-one, 2-benzyl-2-dimethylamino-1-(4-morpholinophenyl)-butane-1-one, 1-(4-dodecylphenyl)-2-hydroxy-2-methylpropane-1-one, 1-hydroxycyclohexylphenylketone, 2-hydroxy-2-methyl-1-phenylpropane-1-one, 1-(4-isopropylphenyl)-2-hydroxy-2-methylpropane-1-one, 2-chlorothioxanthone, 2,4-diethylthioxanthone, 2,4-diisopropylthioxanthone, 2,4-dimethylthioxanthone, isopropylthioxanthone, and 1-chloro-4-propoxythioxanthone.

In addition, a commercially available photopolymerization initiator may also be used. For instance, the following compounds can be preferably used: ketone-based compounds such as IRGACURE 184®, IRGACURE 369® IRGACURE 651®, and IRGACURE 907® (Ciba Specialty Chemicals), DAROCURE® (Merck), and ADEKA 1717® (Asahi Denka. Kogyo Co., Ltd.); and biimidazole-based compounds such as 2,2'-bis(o-chlorophenyl)-4,5,4'-tetraphenyl-1,2' biimidazole (Kurogane Kasei Co., Ltd.). In addition, it is also possible to add a sensitizer, in addition to a photopolymerization initiator, as long as the objective of the present invention is attained.

It is preferable to add a photopolymerization initiator in an amount at which liquid crystal regularity of a polymerizable liquid crystal is not significantly impaired. A photopolymerization initiator can be added to a polymerizable liquid crystal material in a manner such that the material contains the initiator in an amount that is generally 0.01% to 15% by mass, preferably 0.1% to 12% by mass, and more preferably 0.5% to 10% by mass thereof.

A coating solution containing a polymerizable liquid crystal used in the present invention may contain a polymerization inhibitor. With the addition of a polymerization inhibitor, it becomes possible to impart thermal stability to a resulting cured polymerizable liquid crystal layer. Examples of a polymerization inhibitor that can be used include a phenol-based radical chain inhibitor.

A coating solution containing a polymerizable liquid crystal used in the present invention may contain a surfactant. With such a coating solution containing a surfactant, it becomes possible to control liquid crystal orientation in an air interface.

A surfactant is not particularly limited unless the liquid crystal expression of a polymerizable liquid crystal is impaired. Examples thereof include: nonionic surfactants such as polyoxyethylene alkyl ether, polyoxyethylene alkylallyl ether, a polyoxyethylene derivative, a polyoxyethylene/polyoxypropylene block copolymer, polyoxyethylene sorbitan fatty acid ester, polyoxyethylene sorbitol fatty acid ester, polyoxyethylene fatty acid ester, and polyoxyethylene alkylamine; and anionic surfactants such as fatty acid salt, alkyl sulfate, alkylbenzene sulfonate, alkylnaphthalene sulfonate, alkyl sulfosuccinate, alkyl diphenyl ether disulfonate, alkyl phosphate, polyoxyethylene alkyl sulfate, a naphthalenesulfonate-formalin condensate, a special polycarboxylic acid-type high-molecular surfactant, and polyoxyethylene alkyl phosphate.

A surfactant can be added to a polymerizable liquid crystal material in a manner such that the material contains the surfactant in an amount that is generally 0.01% to 1% by mass, preferably 0.05% to 0.5% by mass thereof.

Regarding a polymerizable liquid crystal, if necessary, a coating solution can be obtained by dissolving the above components in a solvent. A solvent that can be used is not particularly limited as long as it can dissolve a polymerizable liquid crystal and each component. Preferably, an organic solvent can be used. In a case in which a coating film is uniformly formed on a base material by a spin coating method, preferred examples of a solvent that can be used include methoxybutyl acetate, diethylene glycol dimethyl ether, propylene glycol monomethyl ether acetate, and cyclohexanone.

A cured polymerizable liquid crystal layer formed as described above has a molecular oriented surface. Thus, a phase difference is generated upon light incidence. A phase difference is determined based on a retardation amount; namely, the product of the birefringent index ($\Delta n$) and the film thickness of the liquid crystal layer. The retardation value can be measured with the use of a commercially available measurement apparatus such as KOBRA-21® (Oji Scientific Instruments). A measurement wavelength is preferably within the visible light region (380 to 780 nm). More preferably, measurement is carried out at around 550 nm, at which the largest relative luminous efficiency is obtained. In addition, in many cases, the retardation value of a coating film having no orientation obtained by applying a polymerizable liquid crystal, followed by UV curing, is 10 nm or less. Thus, it can be said that a cured polymerizable liquid crystal layer has a molecular orientation when the retardation value is 10 nm or more, more preferably 30 nm or more.

In addition, preferably, the surface of a cured polymerizable liquid crystal layer has appropriate hydrophilicity. The hydrophilicity or water repellency of the surface of a cured polymerizable liquid crystal layer can be evaluated by measuring the water contact angle. The water contact angle is a value measured by a static contact angle measurement method, comprising depositing small droplets on the surface of a material under normal atmospheric pressure with the use of a tool such as a syringe and observing an angle made between the gas-liquid interface and the solid face at a droplet edge with the use of a magnifying glass or the like. For instance, such measurement can be carried out with a water contact angle meter (Kyowa Interface Science Co., Ltd.) or the like. In general, the hydrophilicity or water repellency on a surface used for cell culture influences adhesion of cells to the surface. Therefore, when the surface of a cured polymerizable liquid crystal layer has appropriate hydrophilicity, it is possible to avoid adhering difficulty for cells to the surface or to prevent cells from dying while floating without adhering to the surface. The water contact angle on the surface of a cured polymerizable liquid crystal layer of the present invention is preferably 55° to 80°, for example. However, such range can vary depending on materials and the like.

The film thickness of a cured polymerizable liquid crystal layer is generally approximately 0.1 to 10.0 µm; however, it is not limited thereto. As long as the objective of the present invention is attained, such layer may have any thickness.

Next, culture of cardiomyocytes on a cardiomyocyte culture support prepared as described above is described below.

For instance, primary mammalian cardiomyocytes prepared by a conventional method can be used as cardiomyocytes to be cultured. Examples of relevant mammals include primates such as humans and monkeys, rodents such as mice, rats, and rabbits, pet animals such as dogs and cats, and farm animals such as cattle, horses, and pigs. Specifically, such primary cardiomyocytes that can be used are cells collected from a newborn mammal and subjected to connective tissue treatment with collagenase. As a method for preparing primary cardiomyocytes, known methods described in different papers can be used (e.g., primary newborn rat cardiomyocytes described in Kinugawa K, Shimizu T, Yao A, Kohmoto O, Serizawa T, Takahashi T., Transcriptional regulation of inducible nitric oxide synthase in cultured neonatal rat cardiac myocytes, Circ Res. 1997; 81: 911-921). Cardiomyocytes to be cultured may be mixed with non-cardiomyocytes (e.g., vascular endothelial cells and fibroblast cells) as long as a cultured cell aggregate has functions of myocardial tissue.

Cardiomyocytes can be cultured by adding an appropriate medium to a vessel containing a cell culture support on the bottom thereof and seeding cardiomyocytes thereon, followed by culturing. Thus, a cardiomyocyte-adherent substrate comprising the cardiomyocyte culture support of the present invention on the surface of which cells have adhered can be obtained. Such cardiomyocyte-adherent substrate has a cured polymerizable liquid crystal layer having a molecular oriented surface. In addition, cardiomyocytes have adhered to the surface. The beating direction of cardiomyocytes is controlled by the molecular orientation on the surface of such cured polymerizable liquid crystal layer. A cardiomyocyte aggregate is formed within 3 to 4 days, in general, after the initiation of culture following seeding. When cardiomyocytes to be cultured are mixed with non-cardiomyocytes, functions of the cardiomyocytes might be inhibited as a result of excessive growth of non-cardiomyocytes after a long culture period. Thus, the culture period is preferably approximately 1 week or less. The thus obtained cardiomyocyte aggregate is controlled in terms of beating direction. Such myocardial aggregate that can beat in a single direction is preferably applied to patch plasty in the case of a heart experiencing heart failure for beating control, and thus it can be used for myocardial regenerative therapy.

EXAMPLES (1) Preparation of Cardiomyocyte Culture Supports

A culture support A (control) was prepared as a cardiomyocyte culture support by applying a coating solution containing a polymerizable liquid crystal and a levelling agent to a base material so as to form a coating film, followed by curing. In addition, a culture support B with its outermost surface serving as an oriented surface was prepared by applying a coating solution containing a polymerizable liquid crystal (but not a levelling agent) to a base material so as to form a coating film, followed by curing.

A base material obtained by forming an oriented film on a glass substrate was used. A polyimide resin (AL1254®, JSR Corporation) was applied to a 100×100 mm glass substrate with a spin coater such that the resulting film thickness became 0.065 followed by calcining in an oven at 230° C. for 1 hour. Subsequently, an oriented film was formed by subjecting the polyimide film on the substrate to a rubbing treatment.

A coating solution having the relevant composition listed in table 1 below was applied with the use of a spin coater to a base material (rubbing base material) prepared by forming an oriented film on the corresponding glass substrate by a rubbing treatment such that the film thickness after calcining became approximately 0.8 μm.

TABLE 1

|  | Culture support A | Culture support B |
|---|---|---|
| Polymerizable liquid crystal (LC242®: BASF) | 24.69 parts by weight | 24.70 parts by weight |
| Solvent (methoxybutyl acetate:cyclohexanone = 3:1) | 74.04 parts by weight | 74.06 parts by weight |
| Photopolymerization initiator (IRGACURE 907®: Ciba Specialty Chemicals) | 1.23 parts by weight | 1.23 parts by weight |
| Levelling agent (BYK 361®: BYK Chemical) | 0.03 parts by weight | — |
| Polymerization inhibitor (di-tert-p-cresol) | 0.01 parts by weight | 0.01 parts by weight |

In addition, a polymerizable liquid crystal LC242® used herein has the structure represented by the following formula.

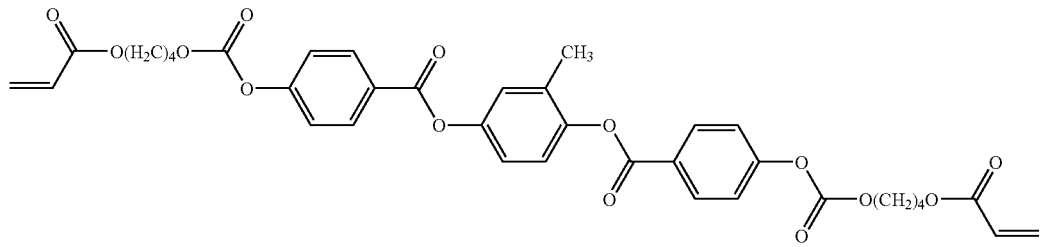

Next, each substrate was retained at 65° C. for 3 minutes such that a polymerizable liquid crystal became a liquid crystal phase. The substrate was dried at 40° C. and under reduced pressure $1 \times 10^2$ Pa for 1 minute. Phase transition to a liquid crystal phase was confirmed based on an increase in transparency of the coating film. The polymerizable liquid crystal in such state was irradiated with ultraviolet rays with the use of an ultraviolet irradiation apparatus and cured by three-dimensional crosslinking. The irradiation dose was 300 mJ/cm$^2$ (365 nm). Thus, a cured polymerizable liquid crystal layer was formed on each base material.

(2) Evaluation

The phase difference (retardation) of each obtained culture support was measured with the use of KOBRA-21® (Oji Scientific Instruments). Measurement was carried out at 550 nm. The retardation in the normal line direction with respect to a culture support was approximately 200 nm in the case of the culture support A, and it was approximately 100 nm in the case of the culture support B. Thus, the culture support B prepared via application of a coating solution containing a polymerizable liquid crystal (but not a levelling agent) was found to have a molecular orientation that can sufficiently influence cardiomyocytes when they are cultured on the surface thereof, even though the culture support B was inferior to the culture support A prepared via application of a coating solution containing a polymerizable liquid crystal and a levelling agent in terms of phase difference value.

Further, the water contact angle of the surface of each obtained culture support was measured at room temperature with the use of a water contact angle meter (Kyowa Interface Science Co., Ltd.). For a control case, a base material (rubbing base material) having an oriented film to which a coating solution had not yet been applied was subjected to measurement in the same manner. The culture support A showed a high contact angle measurement of 81.6° such that it exhibited water repellency. The rubbing base material showed a rather low contact angle measurement of 61.6°. On the other hand, the culture support B showed a medium-level contact angle measurement of 71.6°. Accordingly, it was found that the culture support B has appropriate hydrophilicity, thereby allowing cells to adhere thereto so as to be cultured.

(3) Culture, Observation, and Measurement of Mouse Primary Cardiomyocytes

Mouse primary cardiomyocytes were collected and prepared by the method of "Y. Haraguchi et al., Biomaterials 27 4766 (2006) 4765-4774." The cells were seeded on the culture supports A and B in an amount corresponding to ¼ of the amount sufficient for them to become confluent. Culture was carried out in a chamber in the presence of 5% $CO_2$ at 37° C. for 4 days. Further, for control cases, a base material (rubbing base material) having an oriented film to which a coating solution had yet not been applied and a plastic culture petri dish were subjected to culture in the same manner.

As a result, beating in random directions was observed in the cases of cardiomyocytes cultured on the culture support A on which the surface of a cured polymerizable liquid crystal layer had been covered with a levelling agent, of those cultured on the rubbing base material having no cured polymerizable liquid crystal layer, and of those cultured on a plastic culture petri dish. Meanwhile, in the case of the culture support B on which the surface of a cured polymerizable liquid crystal layer had not been covered with a levelling agent, many cardiomyocytes were observed to dilate and contract during beating in the molecular orientation direction on the surface of the cured polymerizable liquid crystal layer under microscopic observation.

In addition, in the case of the rubbing base material, the strongest cell adhesion/spreading was observed, while on the other hand, the weakest beating was observed. Meanwhile, in the case of the culture support having a cured polymerizable liquid crystal layer, though cell adhesion/spreading was not as strong as in the case of the rubbing base material, spontaneous beating of cardiomyocytes similar to that in the case of the plastic culture petri dish was observed.

A motion video of contracting cardiomyocytes was recorded (1/30 s) under a microscope. The video was analyzed with the software that can identify interframe difference (see "Toshio Modegi, Journal of Medicine (2004) 24 (1) 193-201"). Beating transmission was observed. In addition, it was possible to visualize the beating direction in an image of the difference generated in an area in which cells significantly contracted upon beating (FIG. 1). In addition, optical influences were noted regarding the microscopic observation of a base material and a culture support each having a phase difference. However, as a result of measurement and observation at positions of 0°, 45°, and 90° and comparison of the results, the beating direction was found to rotate relative to the relevant position. Accordingly, it was judged that there was no optical influence.

Further, cardiomyocytes were seeded on the culture support B in an amount corresponding to 1/16 of the amount sufficient for them to become confluent. Culture was carried out under the same conditions for 4 days. A motion video recorded during the 4 days after seeding was analyzed. Accordingly, many spherical unspread cells were observed to beat. In addition, in the case of beating cells in an early phase of cell spreading during which cell migration became moderate, most cells were found to beat in the molecular orientation direction. When cell spreading advanced, beating was terminated. Cells that were confirmed to be cardiomyocytes tended to spread in a direction corresponding to the molecular orientation of a cured polymerizable liquid crystal layer. Such cells were found to beat in a single direction when beating restarted in a late phase of spreading.

Myoblasts differentiated from a precursor were seeded on a culture support B in an amount sufficient for them to become confluent, followed by culture. They were oriented in the molecular orientation direction of the culture support.

A culture support described above was prepared as the cardiomyocyte culture support of the present invention and culture of mouse primary cardiomyocytes was carried out thereon under different conditions. Accordingly, cardiomyocytes capable of dilating and contracting upon beating in a molecular orientation direction on the surface of a cured polymerizable liquid crystal layer were obtained.

All references, including any publications, patents or patent applications cited in this specification are hereby incorporated by reference in their entirely.

What is claimed is:

1. A cardiomyocyte cell culture support system comprising:
    a cardiomyocyte cell layer, and
    a base material coated with a continuous layer of a cured polymerizable liquid crystal having a molecular orientation on a flattened surface thereof,
    wherein the cardiomyocyte cells in said cell layer are attached to and aligned with the molecular orientation at the surface of said continuous layer of the cured polymerizable liquid crystal, and
    a water contact angle on the surface of the cured polymerizable liquid crystal layer ranges from 55° to 80°,
    wherein the base material has orientation ability and comprises a substrate and an oriented film on the substrate, and the cured polymerizable liquid crystal layer is formed on the oriented film.

2. The cardiomyocyte cell culture support system according to claim 1, wherein the continuous layer of cured polymerizable liquid crystal comprises nematic liquid crystal having at least two polymerizable groups in each liquid crystal molecule.

* * * * *